(12) United States Patent
Melker et al.

(10) Patent No.: US 8,525,666 B2
(45) Date of Patent: Sep. 3, 2013

(54) HANDWASHING COMPLIANCE DETECTION SYSTEM

(75) Inventors: Richard J. Melker, Gainesville, FL (US); Nikolaus Gravenstein, Gainesville, FL (US); Donn Michael Dennis, Gainesville, FL (US); Christopher Batich, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 523 days.

(21) Appl. No.: 12/599,743

(22) PCT Filed: Jun. 9, 2008

(86) PCT No.: PCT/US2008/066329
§ 371 (c)(1),
(2), (4) Date: Jun. 29, 2010

(87) PCT Pub. No.: WO2008/154494
PCT Pub. Date: Dec. 18, 2008

(65) Prior Publication Data
US 2010/0265059 A1 Oct. 21, 2010

Related U.S. Application Data

(63) Continuation-in-part of application No. 11/760,100, filed on Jun. 8, 2007, now Pat. No. 7,755,494.

(51) Int. Cl.
*G08B 1/08* (2006.01)

(52) U.S. Cl.
USPC .................. 340/539.11; 340/528; 340/573.1; 340/573.6; 340/539.12; 340/632; 424/70.1

(58) Field of Classification Search
USPC ................ 340/573.1, 539.11, 539.12, 573.6; 424/70.1
See application file for complete search history.

(56) References Cited

U.S. PATENT DOCUMENTS

| | | | |
|---|---|---|---|
| 4,706,493 | A | 11/1987 | Chang et al. |
| 5,610,589 | A | 3/1997 | Evans et al. |
| 5,793,653 | A | 8/1998 | Segal |
| 5,952,924 | A | 9/1999 | Evans et al. |

(Continued)

FOREIGN PATENT DOCUMENTS

| | | |
|---|---|---|
| GB | 2 324 397 | 10/1998 |
| GB | 2 417 811 | 3/2006 |

(Continued)

OTHER PUBLICATIONS

Boyce, John M., et al., "Guideline for Hand Hygiene in Health-Care Settings," *MMWR Recommendations and Reports*, Oct. 25, 2002, 51(RR16);1-44.

*Primary Examiner* — Tai T Nguyen
*Assistant Examiner* — Ojiako Nwugo
(74) *Attorney, Agent, or Firm* — Thomas | Horstemeyer, LLP (57) ABSTRACT

Systems and methods are provided for monitoring use of handwashing agents to determine compliance with hand hygiene guidelines. A handwashing agent is provided with a detectable, volatile compound, such as odors, which is then rubbed onto a subject's hands using the subject's handwashing technique. After the handwashing event, the subject's hand is then exposed to an detector (such as a badge), which includes a sensor capable of detecting the volatile compound, and an indicator that communicates detection of the volatile compound, indicating use of the handwashing agent and hand hygiene compliance.

10 Claims, 3 Drawing Sheets

(56) References Cited

U.S. PATENT DOCUMENTS

| | | | |
|---|---|---|---|
| 6,009,333 A | 12/1999 | Chaco | |
| 6,038,331 A * | 3/2000 | Johnson | 382/100 |
| 6,154,139 A | 11/2000 | Halle | |
| 6,211,788 B1 | 4/2001 | Lynn et al. | |
| 6,236,317 B1 | 5/2001 | Cohen et al. | |
| 6,392,546 B1 | 5/2002 | Smith | |
| 6,417,773 B1 | 7/2002 | Vlahos et al. | |
| 6,426,701 B1 | 7/2002 | Levy et al. | |
| 6,524,390 B1 | 2/2003 | Jones | |
| 6,572,564 B2 | 6/2003 | Ito et al. | |
| 6,647,649 B2 | 11/2003 | Hunt et al. | |
| 6,727,818 B1 | 4/2004 | Wildman et al. | |
| 6,838,992 B2 | 1/2005 | Tenarvitz | |
| 6,882,278 B2 | 4/2005 | Winings et al. | |
| 6,970,574 B1 | 11/2005 | Johnson | |
| 7,015,816 B2 | 3/2006 | Wildman et al. | |
| 7,034,677 B2 | 4/2006 | Steinthal et al. | |
| 7,095,501 B2 | 8/2006 | Lambert et al. | |
| 7,171,312 B2 | 1/2007 | Steinthal et al. | |
| 7,236,097 B1 | 6/2007 | Cunningham | |
| 7,286,057 B2 | 10/2007 | Bolling | |
| 7,375,640 B1 | 5/2008 | Plost | |
| 7,408,470 B2 | 8/2008 | Wildman et al. | |
| 7,443,305 B2 | 10/2008 | Verdiramo | |
| 7,482,936 B2 | 1/2009 | Bolling | |
| 2004/0001009 A1 | 1/2004 | Winings et al. | |
| 2006/0071799 A1 | 4/2006 | Verdiramo | |
| 2006/0273915 A1 | 12/2006 | Snodgrass | |
| 2007/0008146 A1 | 1/2007 | Taylor et al. | |
| 2007/0008149 A1 | 1/2007 | Bolling | |
| 2007/0015552 A1 | 1/2007 | Bolling | |
| 2007/0020212 A1 | 1/2007 | Bernal et al. | |
| 2007/0215000 A1 * | 9/2007 | Reybuck et al. | 106/18.33 |
| 2008/0031838 A1 * | 2/2008 | Bolling | 424/70.1 |

FOREIGN PATENT DOCUMENTS

| | | |
|---|---|---|
| GB | 2417811 | 8/2006 |
| GB | 2 425 388 A | 10/2006 |
| JP | 62132161 | 6/1987 |
| JP | 2001292918 | 10/2001 |

* cited by examiner

Isotopes Relevant to the Indicating Hand Washing event

| Isotope | Stable, Non-radioactive | Radioactive, Unstable |
|---|---|---|
| Hydrogen | $^1H$ (protium) – 99.985%<br>$^2H$ (deuterium) = $^2H$ – 0.015% | $^3H$ (tritium) |
| Carbon | $^{12}C$ – 98.89%<br>$^{13}C$ – 1.11% | $^{14}C$ |
| Oxygen | $^{16}O$ – 99.759%<br>$^{17}O$ – 0.037% [MRI scans]<br>$^{18}O$ – 0.204% [PET scans] | $^{15}O$<br>$^{19}O$ |
| Nitrogen | $^{14}N$ – 99.63%<br>$^{15}N$ – 0.37% [biochemical tracers] | No convenient |
| Sulfur | $^{32}S$ – 95.00%<br>$^{33}S$ – 0.76%<br>$^{34}S$ – 4.22%<br>$^{36}S$ – 0.014% | $^{35}S$ (other S-based radioisotopes very short lived) |

FIG. 3

HANDWASHING COMPLIANCE DETECTION SYSTEM

CROSS-REFERENCE TO RELATED APPLICATION

This application is a continuation-in-part of PCT/US08/066329 filed Jun. 9, 2008, which is a continuation-in-part of U.S. patent application Ser. No. 11/760,100 filed Jun. 8, 2007, the disclosures of which are hereby incorporated by reference in their entirety.

BACKGROUND OF THE INVENTION

Tens of thousands of people die each year from infections acquired in hospitals. These "hospital acquired" infections, also referred to as nosocomial infections, are unrelated to a patient's initial hospital admission diagnosis. In the United States, it has been estimated that as many as one hospital patient in ten acquires a nosocomial infection, or 2 million patients a year. Estimates of annual costs related to nosocomial infection range from $4.5 billion to $11 billion and up. Studies have shown that at least one third of nosocomial infections are preventable.

Nosocomial infections due to resistant organisms are an extremely serious problem that threatens the U.S. healthcare system and the welfare of its citizens. Microbes can acquire resistance to antibiotics and antifungal and antiviral agents and as the numbers of resistant organisms increase, the number of new antimicrobial agents to treat them has not kept pace. In fact, community acquired nosocomial infections, especially methicillin resistant *staphylococcus aureus* (MRSA), have increased at an alarming rate.

It is has been reported that more than 50% of all nosocomial infections can be directly related to the transmission of harmful bacteria by healthcare workers who have not properly washed their hands before and after each patient contact. Thus, the best means to prevent transfer of these organisms from patient to patient and to reduce the emergence of resistant organisms is handwashing with soap and water between patient contacts. The Centers for Disease Control and Prevention (CDC) as well as other regulatory agencies recommend handwashing before and after each patient encounter. Unfortunately, reports indicate that healthcare workers adhere to handwashing guidelines less than 70% of the time. See O'Boyle, C. A. et al., "Understanding adherence to hand hygiene recommendations: the theory of planned behavior," *Am J Infect Control.*, 29(6):352-360 (2001). Numerous strategies have been attempted to increase healthcare worker compliance to handwashing, but all have been largely unsuccessful.

There are many possible reasons for non-compliance with recommended handwashing practices. For example, there may not be sufficient time to properly wash hands or wash stations may be placed in inconvenient locations. Some people simply forget to wash their hands. Others may not realize how infrequently or inadequately they comply with recommended handwashing practices. Others still may not fully understand the benefits of handwashing. Some or all of these issues may be addressed if means were provided to monitor compliance with recommended handwashing practices.

The problem of insufficient handwashing is becoming worse. Hospitals, through staff reductions, are requiring healthcare workers to attend to more patients during the healthcare provider's work shift. Additionally, high transmission rates of antibiotic resistant bacteria and viruses require greater adherence to the CDC handwashing guidelines. Hospital administrations are searching for products and services that encourage handwashing, and a means to ensure and measure compliance.

Similar concerns exist in other industries, such as those relating to the processing and preparation of food. The U.S. Food and Drug Administration's Food Code (the "Food Code") provides guidelines for preparing food and preventing food-borne illness. Retail outlets such as restaurants and grocery stores and other institutions such as nursing homes are subject to the Food Code. In addition to requiring employees to wash their hands, the Food Code requires their employer to monitor the employees' handwashing. Despite such extensive efforts to ensure that proper handwashing is performed, more than a quarter of all food-borne illnesses (estimated that food-borne diseases cause approximately 76 million illnesses, 325,000 hospitalizations, and 5,000 deaths in the United States each year) are thought to be due to improper or insufficient handwashing.

Numerous inventions such as touch-free, automatic soap dispensers, faucets and hand dryers attempt to address the problem of workplace hygiene by making it easier for employees to wash and sanitize their hands. For example, U.S. Pat. No. 5,945,910 teaches systems and methods in which the dispensing of cleaning agents at a washstation are monitored, where the dispensing of cleaning agents is considered an indication of a handwashing event. Another approach is taught in U.S. Pat. No. 4,896,144 which, although not designed for measuring or checking handwashing compliance, is directed to alerting someone of the need to wash their hands. U.S. Pat. No. 5,812,059 is directed to a method and system for improving hand cleanliness, primarily in a food service environment. It discloses a reporting means worn by a worker, which is activated when the worker leaves a food handling area. The reporting means, worn by the worker, is deactivated by a deactivating device associated with a hand cleaning station, and only when it is determined that the worker has used the hand cleaning station before re-entry to the food handling area.

Even with the monitoring systems described above, unless employees are actively supervised in the washroom, however, there is usually no way to determine whether they have washed their hands. Furthermore, if the employees do wash their hands, there is no way to easily determine whether they have followed a prescribed government- and/or industry-approved regimen to ensure they washed and sanitized properly.

BRIEF SUMMARY OF THE INVENTION

The subject invention solves the needs in the art by providing systems and methods for monitoring and promoting hand hygiene practices. According to the subject invention, a system for promoting adherence to handwashing (or hygiene) guidelines comprises: a handwashing agent that includes a detectable, volatile or semi-volatile compound (also referred to herein as the "handwashing adherence marker" or HWAM), and a detector (such as a badge) that includes a sensor for detecting the HWAM and an indicator operatively connected to the sensor that provides a signal indicating detection of the HWAM. The HWAM can comprise a chemical found in handwashing media (e.g., an added compound or a chemical already part of the commercial formulation, hereafter referred to as "taggants") or a molecular entity derived from conversion (e.g., including but not limited to metabolism in skin) of a chemical found in the handwashing media. Thus, the HWAM(s) may be the taggant itself, a metabolite of the taggant, or combinations thereof. In addition, the handwashing system may utilize more than one handwashing adherence markers (HWAMs).

An object of the subject invention is to detect the HWAM arising from a subject's hands, wherein the presence of the HWAM is an indication of subject compliance in hand hygiene activities. In one preferred embodiment, the HWAM is a compound that is inconspicuous, so that when a subject applies the handwashing agent to one's hands, the HWAM is essentially undetectable to the subject's olfactory senses during and after the handwashing event. More preferably, the HWAM is detectable on the skin through the use of a sensor of the invention, even if the handwashing agent is removed via rinsing, rubbing, and/or drying. In certain embodiments, the HWAM is an FDA approved perfume and/or fragrance.

In operation of an embodiment, a subject (e.g., a healthcare provider or an employee of a restaurant) is provided with a detector (e.g., a badge) that is worn during working hours. The detector is designed to remind or alert the subject (or other interested parties, such as a monitoring agent, a customer, or a patient) regarding whether the subject has washed his/her hands. Alternatively, the detector is not worn, and for example can be positioned in close proximity to a handwashing station, including a sink with exogenous (e.g., tap) water-requiring handwashing media (e.g., soap and water, Hibiclens) or the site of non-exogenous water requiring handwashing media (e.g., gel or foam handwashing agents). The detector contains the necessary sensor to detect the HWAM(s) as well as an indicator to receive and communicate information from the sensor. After a handwashing event, HWAM(s) from the handwashing agent are detected on, or emanating from, the subject's hands using the sensor. If the HWAM is detected, the indicator will communicate detection of the compound constituting the HWAM, which is a sign of subject performance in handwashing.

A resulting advantage of the subject invention is the ability to monitor hand hygiene compliance in a more cost effective and frequent manner than current systems and methods, which can involve expensive and bulky equipment.

Additional advantages of this invention will become readily apparent from the ensuing description.

DETAILED DESCRIPTION OF THE INVENTION

The present invention provides systems and methods for monitoring hand hygiene activities performed by a subject by detecting a HWAM on, or emanating from, the subject's skin, where the taggant, which generates the HWAM, is present in a handwashing agent. In some instances, the taggant can be the propellant already included in the commercially marketed product, particularly if it produces foam. The systems and methods of the invention can be practiced in any institution where hand hygiene is important. Examples of such institutions include, but are not limited to, hospitals and other health care facilities, nursing homes, restaurants and other food service institutions, food processing and manufacturing institutions, libraries, schools, airports, and the like.

A hand hygiene monitoring system of the invention comprises a handwashing agent that includes a taggant, which may be the propellant or other ingredient already present in the agent or a compound added specifically because it is detectable by a specific type of sensor; and a detector that includes a sensor and an indicator. The system of the invention monitors hand hygiene compliance by detecting when a subject washes or rubs his/her hands with a handwashing agent that includes the taggant to generate the HWAM. Preferably, the HWAM is detectable using the sensor after appropriate hand hygiene measures are taken by the subject. An indicator that is operatively connected to the sensor communicates to the subject (and/or any other interested party such as a patient or customer) whether a handwashing event has occurred within a prescribed interval. In certain embodiments, the hand hygiene monitoring system further includes a means for storing information regarding the handwashing event (e.g., storage of information regarding identity of the subject, time of handwashing event, compliance/non-compliance in handwashing event, etc.).

A method for monitoring hand hygiene compliance involves detecting the presence or absence of a HWAM arising from the subject's skin using a detector containing a sensor; and communicating whether the HWAM is present on the subject's skin using an indicator. The method can include storing and analyzing the occurrence of HWAM detection (data) using a computing means. Data regarding HWAM detection may be used to determine subject history (log) in hand hygiene compliance or percentage of hand hygiene compliance. In addition, the method may involve communicating whether the subject has washed his/her hands within a period of time subsequent to detection of the presence of a HWAM. If a subject does not comply with appropriate hand hygiene measures, which includes using a handwashing agent that has a taggant to generate the HWAM, the method may also involve triggering a reminder alarm using the indicator.

Definitions

As used herein, the term "handwashing" or "hand hygiene" (which can be used interchangeably), refers to washing hands with a handwashing agent and water or applying a handwashing agent to surfaces of the hand. Handwashing can include dipping hands into a handwashing agent or friction-generating activities, such as those accompanying the use of surgical scrubs that "stir up the dermis" and get down at least 3-5 cell layers.

As used herein, the term "handwashing agent" refers to a substance used in maintaining hand hygiene (e.g., reducing the number of microorganisms on the skin). A handwashing agent of the subject invention includes, but is not limited to, alcohol-based hand rubs; antimicrobial and/or antiseptic soaps; antiseptic hand washes; antiseptic hand rubs; detergents; soaps; waterless antiseptic agents; and surgical hand scrubs. A handwashing agent may be in the form of a solid (e.g., bar of soap, surgical prep sponge), powder, liquid, cream, spray, gel, or the like.

According to the subject invention, an alcohol-based hand rub is an alcohol-containing preparation designed for application to the hands for reducing the number of viable microorganisms on the hands. Such preparations can contain about 60%-95% ethanol, isopropanol, n-propanol, or any combination of these compounds.

As used herein, an antimicrobial soap refers to a product comprising soap or detergent and an antiseptic agent.

As used herein, an antiseptic agent refers to antimicrobial substances that are applied to the skin to reduce the number of microbial flora. Examples of antiseptic agents include alcohols, chlorhexidine, chlorine, hexachlorophene, iodine, chloroxylenol (PCMX), quaternary ammonium compounds, and triclosan.

As used herein, a detergent or soap is a product that includes compounds that possess a cleaning action. They are composed of both hydrophilic and lipophilic parts and can be divided into four groups: anionic, cationic, amphoteric, and nonionic detergents. Although products used for handwashing or antiseptic handwash in health-care settings represent various types of detergents, the term "soap" also refers to such detergents.

As used herein, a waterless antiseptic agent refers to an antiseptic agent that does not require use of exogenous water. After applying such an agent, the hands are rubbed together until the agent has dried.

As used herein, an antiseptic hand wash or hand rub refers to an antiseptic-containing preparation designed for frequent use; it reduces the number of viable microorganisms on intact skin after washing, rinsing, and drying; it is broad-spectrum, fast-acting, and potentially has a persistent effect.

As used herein, a surgical hand scrub is an antiseptic-containing preparation that substantially reduces the number of viable microorganisms on intact skin; it is broad-spectrum, fast-acting, and persistent. Persistence refers to the duration of time from handwashing until viable organisms again colonize or contaminate the skin in sufficient numbers to be a source of potential infection to a patient, or the time that the HWAM is detectable on or in proximity to the hands after application.

Throughout this disclosure, a HWAM is defined as a substance or a combination of substances that is detected by means of its physical or chemical properties using a sensor of the subject invention. HWAMs preferably remain on the skin for a sufficient time after rinsing or drying for detection by a sensor of the invention. HWAMs are preferably unique in a handwashing agent (for example, they are not molecules commonly present in proximity of the subject in densities sufficient to be detectable by the sensor except in the handwashing agent). In addition, the HWAM(s) and the taggant(s) that generates the HWAM(s), should be non-toxic to the subject; do not alter or impair the anti-microbial, anti-viral, anti-bacterial, and/or anti-septic properties of the handwashing agent; relatively inexpensive; readily available; and easy to synthesize as well as integrate with the handwashing agent. In certain embodiments, halogenated molecules, including perfluorocarbons (PFCs), hydrofluorocarbons (HFCs), or fluoroalcohols, may serve as the handwashing taggant. In some cases, these molecules will already be a component of a commercial handwashing system (e.g., HFC-32 as the propellant in foam-based handwashing systems), or could be added specifically as a taggant to handwashing agents.

Hand Hygiene Monitoring System

The subject invention relates to systems for monitoring hand hygiene compliance that include a handwashing agent with a taggant to generate the HWAM and a detector, which includes a sensor and an indicator. The sensor has the ability to detect HWAMs on a subject's skin or as they emanate from the skin and the indicator communicates detection of the HWAM. Communication regarding HWAM detection can be immediate, as by a visual means and/or audible sound from the indicator. Further, communication regarding HWAM detection can be transmitted or stored in a database, or to another device used to alert others such as healthcare providers, food handlers, patients, or customers that a subject has washed his/her hands.

According to the subject invention, HWAM detection is a surrogate indication of use of the handwashing agent, and thus an indication of a handwashing event. An integral part of a system of the invention involves the communication of whether and/or when a handwashing event has occurred, as derived from monitored detection of HWAMs on or in proximity to the subject's skin, to improve subject compliance in hand hygiene.

Certain embodiments include storing and/or analyzing data regarding HWAM detection (and handwashing event), including intervening with the subject when appropriate to improve compliance. Appropriateness for intervention is dependent upon the number of handwashing events detected over a period of time when compared against an expected number of handwashing events for the same period of time.

In certain embodiments, the detector includes a suction pump for directing air toward the sensors. For example, the suction pump can be used to ensure HWAMs from the skin are director toward the sensor(s) of the detector.

Taggants

The subject invention provides a system that monitors handwashing events. Specifically, handwashing events are monitored based on the detection of HWAMs on or in proximity to a subject's skin, where the HWAM is a surrogate indicator of use of a handwashing agent. According to the subject invention, handwashing agents include a volatile, semi-volatile, or even non-volatile detectable HWAM. Preferred taggants of certain embodiments of the invention are those compounds that generate HWAMs with sufficient vapor pressure and volatility to be readily detectable shortly after handwashing but that would be undetectable a short time later (e.g., those HWAMs characterized with short persistence times). More preferably, the taggants and the HWAMs, when it is a different molecular entity from the taggant (e.g., when the taggant is chemically transformed to the HWAM by the skin), are safe for frequent use on the skin without the potential for allergic reactions or drying of the skin.

In one embodiment, the taggants are already present in the commercial handwashing agent (e.g., difluoromethane [HFC-32] in foam-based systems). In another embodiment, the taggants are sufficiently miscible in commercial handwashing solutions so they can be directly added to them, including but not limited to adding small quantities of fluorinated alcohols with variable degrees of fluorinated substitutions of H atoms (e.g., ranging from a single F substitution on a H atom on a single $CH_3$ and/or $CH_2$ group to multiple F substitutions on these groups) on molecules commonly found in handwashing agents (e.g., fluorinated versions of ethanol and isopropyl alcohol) or adding novel alcohols such as tertiary or secondary alcohols with various degrees of fluorine substitutions of H atoms such as 1,1,1,3,3,3-Hexafluoro-2-methyl-2-propanol, 1,1,1-Trifluoro-2-methyl-2-propanol; and 1,1,1,3,3,3-Hexafluoro-2-(trifluoromethyl)-2-propanol), as well as 1,1,1,3,3,3-Hexafluoro-2-propanol (HFIP), respectively. In another embodiment, a taggant(s) is added to the handwashing media by localizing it within hard (e.g., microencapsulation techniques) and/or soft particles (e.g., microemulsions and/or micelles). Such taggants are preferably chosen from compounds that are suitable for microencapsulation, coating, or incorporating into dissolvable particles/polymer systems, and would remain stable until released during handwashing. Such embodiments would require vigorous handwashing by the subject, and in some cases, exposure to water, to release the taggant.

There are also many ways to incorporate taggants into water-dispersible polymers. Microencapsulated particles used to house taggants can be made using standard microencapsulation techniques including, but not limited, coacervation (e.g., complex coacervation), double emulsion (w/o/w), polymerization (e.g., interfacial, in-situ, or matrix polymerization), co-extrusion capsule formulation (e.g., drip mode, centrifugal, or jet mode co-extrusion), and air-suspension coating. For instance, in the double emulsion technique, poly L-lactic acid (PLLA) is dissolved in methylene chloride, and emulsified with an aqueous (or other incompatible solvent) containing the detectable taggant. This is adjusted to make a water in oil emulsion. This emulsion is poured into a second aqueous (or incompatible solvent) and air is bubbled through, which evaporates the organic solvent (methylene chloride), causing the PLLA to encapsulate in a hard shell, the detectable taggant. The skilled artisan would readily understand which polymers, solvents, temperature, stirring rates, and surfactants should be added to optimize properties for detection in a handwashing agent. Capsules can be made to degrade or fracture under different conditions.

Although this particular formulation may not be ideal for all applications, it is presented as a commonly used method of encapsulation. Another example using a similar approach involves mixing a small amount of a taggant such as a fluorocarbon with a surfactant and water with dissolved sugar. The emulsion formed (organic dispersed in a continuous aqueous phase) is then poured into a larger volume of a non-volatile organic liquid such as a silicone oil, and air then is bubbled through this. The resulting particles contain fluorocarbon trapped within a sugar matrix which formed upon evaporation of the water by the air. When suspended in an organic gel (such as isopropanol based), the particles remain intact until they are exposed to water and rubbing caused by the washing of hands. At that point, the sugar dissolves in the new water, and releases the volatile fluorocarbon.

There are a wide variety of ways that the volatile materials can be delivered to the washing milieu upon the act of washing and contact between water and the solutions. Most simply, a pressurized container can be attached to the disinfecting liquid container so that activation of one also releases the contained taggant into the other liquid. Particles can be made using the well known "Scratch and Sniff" methods developed in the 1960's based on either gelatin or a synthetic microencapsulation shell such as the melamine resins. The shell is adjusted to a size and thickness to fracture when rubbed, releasing the contained volatile material. Volatile acids or bases can be made less volatile by forming salts, which then are released when the pH of the medium is changed during washing by loss of a volatile acid or base material which shifts the pH. Water can activate a mixture of dry sodium bicarbonate and dry calcium acetate for instance, which can cause evolution of carbon dioxide and disrupt a microcapsule. Simple osmotic pressure formed by water movement into an encapsulated salt can also disrupt a shell. Volatile acids, such as acetic or butyric acid, can be attached to a polymer with an ester bond which may be cleaved by esterases present naturally or delivered in a two part applicator. There are many ways to fracture or dissolve a shell encapsulating a volatile taggant or mixture, and they can be readily adapted to the specific carrier chosen.

Preferably, the volatile taggant of certain embodiments of the invention generates a HWAM that would readily evaporate and be undetectable by human or electronic senses after a specified period of time (such as within 1 minute or within 1-5 minutes, or within 5-10 minutes) following handwashing. In accordance with the present invention, taggants that are combined with a handwashing agent include the following olfactory taggants, without limitation: dimethyl sulfoxide (DMSO), acetaldehyde, acetophenone, trans-Anethole (1-methoxy-4-propenyl benzene) (anise), benzaldehyde (benzoic aldehyde), benzyl alcohol, benzyl cinnamate, cadinene, camphene, camphor, cinnamaldehyde (3-phenyl-propenal), garlic, citronellal, cresol, cyclohexane, eucalyptol, and eugenol, eugenyl methyl ether; butyl isobutyrate (n-butyl 2, methyl propanoate) (pineapple); citral (2-trans-3,7-dimethyl-2,6-actadiene-1-al); menthol (1-methyl-4-isopropyl cyclohexane-3-ol); and α-Pinene (2,6,6-trimethylbicyclo-(3, 1,1)-2-heptene). These taggants are preferred since they are permitted by the Food and Drug Administration. Olfactory taggants for use in the present invention can be selected from a vast number of available compounds (see *Fenaroli's Handbook of Flavor Ingredients*, 4$^{th}$ edition, CRC Press, 2001) and use of such other applicable taggants is contemplated herein.

The taggants of the invention also include compounds that have been federally approved and categorized as GRAS ("generally recognized as safe"), which are available on a database maintained by the U.S. Food and Drug Administration Center for Food Safety and Applied Nutrition. Taggants categorized as GRAS that are readily detectable using a sensor of the invention include, but are not limited to, sodium bisulfate, dioctyl sodium sulfosuccinate, polyglycerol polyricinoleic acid, calcium casein peptone-calcium phosphate, botanicals (e.g., chrysanthemum; licorice; jellywort, honeysuckle; lophatherum, mulberry leaf; frangipani; selfheal; sophora flower bud), ferrous bisglycinate chelate, seaweed-derived calcium, DHASCO (docosahexaenoic acid-rich single-cell oil) and ARASCO (arachidonic acid-rich single-cell oil), fructooligosaccharide, trehalose, gamma cyclodextrin, phytosterol esters, gum arabic, potassium bisulfate, stearyl alcohol, erythritol, D-tagatose, and mycoprotein.

Figure 3:
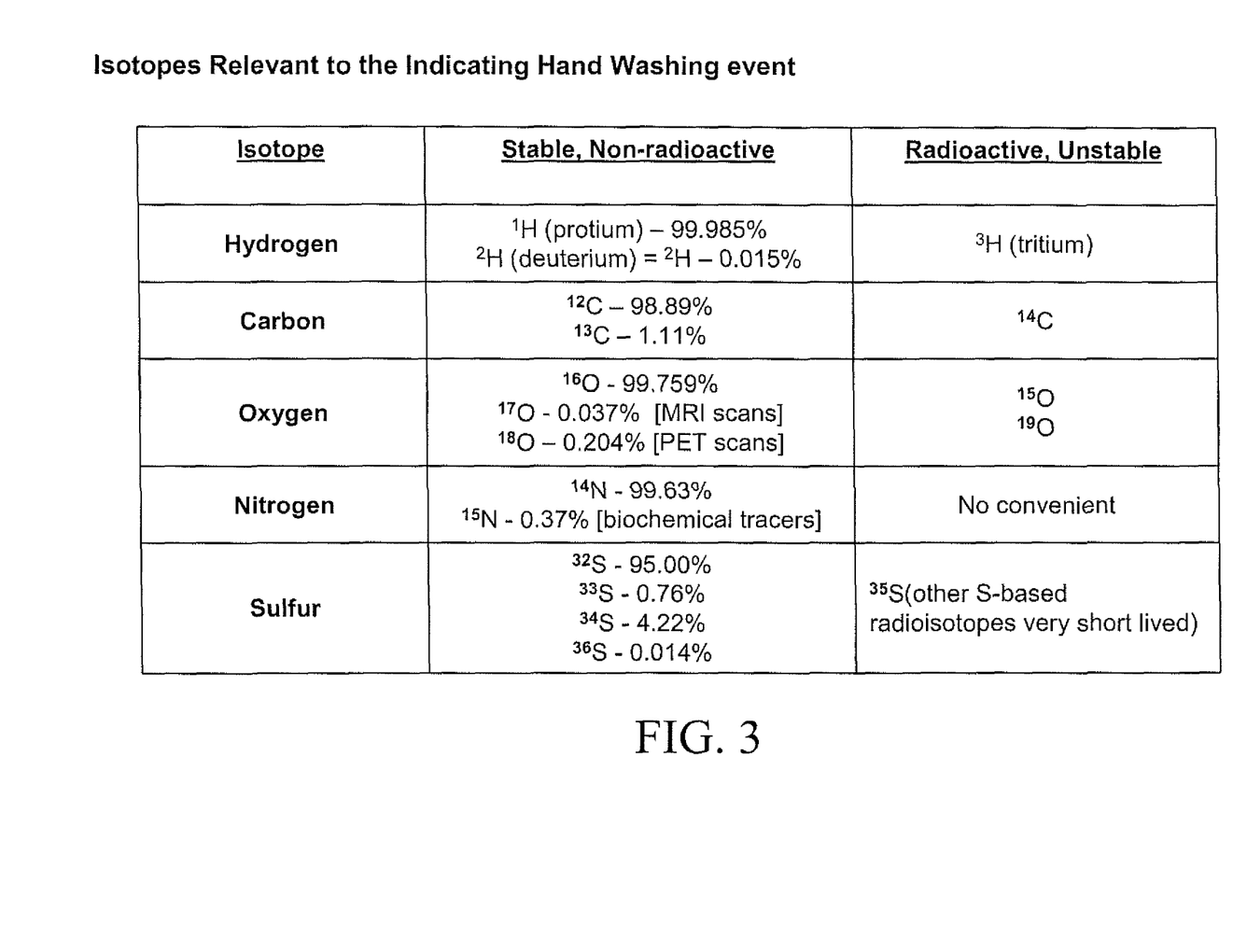
FIG. 3 is a table showing various isotopes that can be used as taggants to generate the HWAM in the subject invention.

Additional taggants of the invention include halogenated compounds (for example, tetrachloroethane, trichloroethane, dichloroethane, dichloroethylene, trifluoroethane (Freon 113), dichloroethane, dichloropropane, 1,3-cis-dichloro-1-propene, 1,3-trans-dichloropropene, 1-chloro-2-propene, butylene dichloride, acetylene tetrachloride, bromodichloromethane, bromoform, bromomethane, carbon tetrachloride, chlorodibromomethane, chloroethane, chloroform, chloromethane, chloropropane, cis-1,2-dichloroethylene, cis-1,3-dichloropropene, dibromo-chloropropane, dibromomethane, dichlorobromomethane, dichloromethane, ethylene dibromide, fluorotrichloromethane (Freon 11), glycerol trichlorohydrin, hexachlorobutadiene, hexachlorocyclopentadiene, hexachloroethane, methylene chloride, neoprene, pentachloroethane, perchloroethylene, propylene dichloride, trichlorotrifluoroethane, monochlorobenzene, tetrachloroethylene (Perchloroethylene) (PCB), trichloroethylene (TCE), vinyl chloride, vinyl trichloride, vinylidene chloride) as well as isotopes, such as those disclosed in FIG. 3.

According to the subject invention, the HWAM can have any one or combination of the following characteristics: (1) HWAM (and taggant, if different from HWAM) has no intrinsic toxicity at concentrations required for detection of the HWAM by a sensor of the invention; (2) HWAM (and taggant, if different from HWAM) is a generally recognized as safe (GRAS) compound; (3) HWAM (and taggant, if different from HWAM) is an FDA approved chemical entity; (4) HWAM is unique on the skin (e.g., not found in non-handwashing agents that are applied to skin), where the HWAM provides an outstanding signal to noise (S:N) ratio with a sensor of the invention, and does not require a baseline reading; (5) HWAM has rapid onset of appearance on or in close proximity to the skin after handwashing by the subject; (6) HWAM has a reproducible duration of appearance on the skin; (7) HWAM is easily detectable by commercially available sensor technologies that are rapid, portable, inexpensive, compact, and available for real-time analysis; and (8) HWAM is generated from a flexible chemistry formulation platform that will allow the selection of optimal taggants with regard to incorporation with handwashing agents and/or time of detection of HWAM on or in proximity to a subject's skin. The one or more taggants present in the handwashing agent can be said to generate a "handwashing adherence marker (HWAM)." The HWAM can be derived from 3 sources: 1) the taggant itself serves as the HWAM and is detected by diffusion of taggant away from the skin; 2) a metabolite of the taggant serves as the HWAM and is detected by diffusion of the metabolite away from the skin; the skin is an enzymatically active organ and contains a wide variety of enzymes; and 3) a metabolite serves as the HWAM and is detected from the metabolite arising from the breath of the individual washing his/her hands; in this case the metabolite that appears in the breath could be due to metabolism by enzymes in the skin and/or by those located outside the integumetary system (e.g., blood, liver). In preferred embodiments, the HWAM is detected from the skin as opposed to the breath.

Using the metabolite of the taggant as the HWAM has advantages, particularly when it is recognized that the skin has an active enzyme machinery. For example, the concentrations of HWAM generated from the taggant will correlate with the extent of handwashing vigor, namely that better handwashing with a fixed amount of taggant in the handwashing media should generate a greater mass of HWAM (e.g., greater surface of skin covered and greater penetration of taggant into the skin where the enzymes catalyze the formation of the HWAM).

The taggant can be present in the handwashing agents (e.g., foam, solution, handwashing wipes, etc.) via three methods: 1) it already exists in the agent media (e.g., fluorocarbons as propellants such as difluoromethane in ethanol-based formulations) of marketed products; 2) it is a new addition to an existing marketed product (e.g., fluorocarbons, hydrofluorocarbons and/or fluoroalcohols added to Hibiclens, Hibistat, Purell, etc.); and 3) it is incorporated into a new product to be used as a handwashing agent.

The taggant can belong to any of a variety of chemical classes. These include but are not limited to the following: 1) compounds designated by the FDA as generally recognized as safe (GRAS) such as those from lists of food additives, inactive ingredients, and/or drug excipients, and 2) compounds designated as being non-GRAS compounds, including existing ones and new chemical entities. Specific chemical classes that could serve as taggants include but are not limited to esters (e.g., parabens), carbonate esters, acetals, ketals, aliphatic higher alcohols, aromatic alcohols, thioalcohols, thiols, fatty acids, aliphatic higher aldehydes, aromatic aldehydes, ethers, thioethers, phenol ethers, ketones, phenols, lactones, terpens, aliphatic higher hydrocarbons, furfurals, indoles, amines, and isothiocyanate.

One chemical class that merits special consideration as a preferred handwashing taggant(s) is halogenated compounds, such as hydro fluorocarbons (HFCs), perfluorocarbons (PFCs), fluoroalcohols, and chloroflurocarbons (CFCs). However, the latter group is not preferred because CFCs destroy ozone molecules. Fluorinated compounds are easily detected by COTS detectors and are harmless to the patient and do not destroy ozone molecules. PFCs, both straight chain and branched entities, relevant to this handwashing technology include but are not limited to tetrafluoromethane ($C_2F_4$), perfluoropropane ($C_3F_8$), perfluoro-n-butane ($C_4F_{10}$) plus other entities including $C_5F_{12}$, $C_6F_{14}$, $C_7F_{16}$, $C_8F_{18}$, $C_9F_{20}$, $C_{10}F_{22}$ and so on. PFCs are fluorocarbons that contain only carbon and fluorine atoms in their chemical structure. Due to the strength of the carbon-fluorine bond and the shielding effect of the fluorine atoms, PFCs are extremely stable, non-toxic, non-flammable, non-carcinogenic, chemically inert molecular entities. Because they have an excellent ability to absorb gases, PFCs have been extensively used in medical applications such as liquid breathing and blood substitutes. In contrast to CFCs, PFCs do not destroy ozone molecules. Likewise, HFCs including but not limited to difluoromethane ($C_2F_2H_2$) can be used according to the subject invention. Compared to PFCs and HFCs, fluoroalcohols are more soluble in water and aliphatic alcohol solutions and have a lower capacity to escape into the atmosphere. Given the molecular structures of PFCs, HFCs, and fluoroalcohols, a variety of physicochemical properties exist (e.g., water solubility, state of matter, boiling point, melting point, Henry's law constant, lipophilicity/hydrophilicity), as well as toxicity profiles, can be exploited to determine the optimal taggant for a particular handwashing situation. In this case, due to their metabolic stability, particularly with the PFCs, the HWAM will generally be the taggant itself. The number of carbon atoms in the PFC molecule will generally dictate the physical properties of the molecule. The greater the number of carbon atoms, the higher the boiling point, density, viscosity, surface tension, critical properties, vapor pressure, and refractive index. Gas solubility decreases as carbon atoms increase. Irrespective of chemical type, factors important to the particular handwashing application, such as how long the HWAM persists and can be detected by the sensor, can be adjusted according to the properties of the taggant.

To improve sensor specificity the taggant may or may not contain non-radioactive non-ordinary isotopic labels.

Using encapsulated approaches that entrap halogenated compounds inside particles, whose release of taggants with physical gating mechanisms (e.g. friction of handwashing causes temperature increases and/or mechanical forces that liberate the taggant) have certain advantages. First, it ensures that the hands were washed vigorously, which directly relates to reduction in the potential for infection. Second, since PFCs are generally not miscible with organic solvents (e.g., ethanol) and water, but are miscible with some hydrocarbons and lipids such as those contained within skin, their release from particles (e.g., hard capsules and/or microemulsions/micelles containing taggant) will generally cause them to rapidly escape from the hands and be detected by the sensor once the particle is broken. Therefore, a strategy of placing fluorinated compounds within a particle (e.g., gated release of PFC and/or HFC contained within microcapsules, microemulsions, or micelles stably suspended in handwashing media via physical stimuli such as increased temperature, mechanical stress secondary to the friction and energy of handwashing, and/or water-induced disruption of microemulsion/micelle stability) is a preferred approach to this handwashing technology.

The taggant in its pure form could exist as a gas, liquid, or solid, or be volatile, semi-volatile, or non-volatile prior to being added to the handwashing solution. The HWAM is preferably detected by the sensor in the gas form, but could also be detected in the liquid form via aerosolization. The handwashing medium can be foam, gel, liquid, etc. The taggant preferably is stably dispersed uniformly in the handwashing medium, and ideally should not require shaking or other forms of agitation to disperse it prior to handwashing.

Detector

The detector of certain embodiments of the invention includes a sensor for detecting the HWAM arising from the subject's skin; and an indicator for reporting whether the HWAM was detected. According to the present invention, the detector can be presented as a badge to be worn by the subject. Preferably, the detector is implemented in a housing structure such as a card-shaped structure, badge-shaped structure, or other compact structure allowing for ease of use, transport, wearability, attachment to a subject, etc. The detector includes a sensor disposed within the badge, where said sensor has the ability to detect the presence of the HWAMs on or in close proximity to the subject's skin (e.g., after the subject has dispensed, soaped, scrubbed, and rinsed his/her hands using a handwashing agent of the invention); and an indicator operably connected to the sensor such that detection of the HWAMs by the sensor is communicated by the indicator to the subject (and/or anyone interested in assessing or monitoring subject hand hygiene).

Preferably, the detector also includes an electronic clock circuit operably connected to the indicator. In one embodiment, the electronic clock continuously generates a time signal based on HWAM detection as communicated by the indicator. For example, using the electronic clock, the indicator can communicate when the last handwashing event occurred. In another embodiment, the electronic clock can be activated when the subject initiates a handwashing event and can communicate via the indicator a specified time that the subject should devote to a handwashing event. For example, the electronic clock can generate a signal for about 5 seconds up to 2 minutes that communicates to the subject the time that should be devoted to handwashing using a handwashing agent).

In certain embodiments, the detector can also include a means for processing data regarding detected HWAM(s)/handwashing event, including a means for storing data regarding handwashing events and for analyzing handwashing events (e.g., comparing the number of handwashing events for a given period of time against expected number of handwashing events for the specified period of time, or against previous recorded handwashing events). Those skilled in the art will appreciate that the processing means may be implemented as electronic hardware, mechanical hardware, computer software, or combinations thereof. Whether the processing means is implemented as hardware and/or software depends upon the particular application and design constraints imposed on the overall system. Skilled artisans may implement these components in varying ways for different applications, but such implementation decisions should not be interpreted as causing a departure from the scope of the subject invention.

According to the present invention, a sensor for use in detecting HWAMs on or emanating from skin can be operatively connected to a data processing system. The processing system is preferably programmed to assimilate and analyze output signals generated by the sensor regarding HWAMs detected on or from the skin. In one embodiment, the processing system is a computer. HWAM analysis results can be displayed on a computer screen, stored, transmitted, etc. Moreover, a computer processing unit (or CPU) may be provided as a data processing/control unit. In one embodiment, the processing unit is programmed for conducting a comparison of data regarding recommended HWAM levels for a specified period of time against monitored HWAM data to determine subject hand hygiene compliance.

For instance, when a physician is scheduled to see twenty patients during a clinic session, forty episodes of handwashing (handwashing should occur both before and after an encounter with a patient) should be recorded in the storage device during the time scheduled for the clinic. Less detected episodes of handwashing are indicative of behaviors that favor nosocomial infection. Likewise, if a physician or other healthcare provider is scheduled to perform a number of procedures (e.g., endoscopy, cystoscopy, bronchoscopy) during a specified time interval, two handwashing episodes, one before and after each procedure, should be detected, stored, and documented.

In one embodiment, the CPU can automatically detect and store signals from the sensor to enable proper tracking and analysis of handwashing events. The CPU may further provide to the subject (or co-workers, patients, customers, etc.) the appropriate alerts regarding handwashing events to be taken either based on pre-entered information or based on analysis of trends in handwashing events.

According to the present invention, a data analyzer can compare a pattern of response (from the sensor) to previously measured and characterized responses from known HWAMs. The matching of those patterns can be performed using a number of known techniques, including artificial intelligence systems (such as neural networks). By comparing analog output from a sensor (based on analyzed HWAMs on or emanating from the skin) to a "blank" or control HWAM output using, for example, a neural network, a pattern can be established that is unique to that HWAM. In one embodiment, the artificial intelligence system can make an assessment of subject compliance with hand hygiene measures. Where appropriate, the artificial intelligence system can also recommend an intervention (such as increased number of handwashing events) to ensure continued subject health and prevent spread of disease due to poor handwashing hygiene.

One conventional approach that can be used in a monitoring system of the invention includes a neural network for processing data obtained from the sensor(s). As with most empirical modeling technologies, neural network development requires a collection of data properly formatted for use. Specifically, as known in the art, input data and/or the outputs of intermediate network processing layers may have to be normalized prior to use. It is known to convert the data to be introduced into a neural network into a numerical expression, to transform each of the numerical expressions into a number in a predetermined range, for example, by numbers between 0 and 1. Thus, the intelligence system of the present invention preferably has means for: 1) selecting at least a portion of the detected HWAM data from the sensor data output signal; 2) converting the selected portion of the detected HWAM data into numerical expressions; and 3) transforming the numerical expressions into a number in a predetermined range.

In accordance with one embodiment of the invention, the intelligence system is trained by providing to a neural network input data regarding expected number of detected HWAM events based on a specified period or part thereof as well as output data from the sensors. The assessment by the intelligence system, along with the corresponding input data and output data is referred to as a data record. All available data records, possibly taken for a number of different subjects (such as male versus female; adult versus pediatric health clinician), comprise a data set. According to the present invention, a data set corresponding is stored in memory and is made available for use by the processing system for statistical, training, and/or diagnostic determinations. Normally, intelligence systems are trained ahead of time using data extracted from subjects. Using what is learned from the training data, the neural network may apply it to other/new subjects.

In other preferred embodiments of the invention, the detector is not worn, but rather is located at a particular location (e.g., at a handwashing station, near a dispenser for handwashing agent, at a door to a patient's room, at a door to a kitchen, and the like) such that the frequency of handwashing can be compared to the frequency of entry to specific locations (e.g., entering patient access areas).

In such embodiments, a means for ascertaining subject identity is provided (e.g., by providing a code specific to the subject). Examples of identity ascertaining means include, but are not limited to, a keypad to be operated by the subject, a barcode reader, a magnetic strip reader, or any other suitable identifying device, such as radio-frequency identification (RF-ID) technology. If the identity ascertaining means is a keypad, it should be capable of receiving codes identifying the subject. The keypad can be of any commonly available alphanumeric design known in the art. If the identity ascertaining means is a barcode reader, RF-ID, or magnetic strip reader, a card or badge containing a barcode, radio-frequency identification, or magnetic strip would be issued to each subject. The subject would place the barcode, radio-frequency identification, or magnetic strip in front of or into the reader to allow the identity ascertaining means to determine the identity of the subject. In other embodiments, biometric devices (fingerprint readers, retinal scanners, etc.) can be used but are in some circumstances less desirable because the user may have to touch the device or its use may increase the time between patient visits).

At each particular location (e.g., entrance of a restroom), the identity ascertaining means will notify a central computer system when a subject enters, and will wait for the subject to wash his/her hands before leaving. After the subject performs appropriate handwashing measures (e.g., applies the proper amount of a handwashing agent of the invention that includes taggants to generate the HWAM, rubs hands together to generate the appropriate lather), the subject waves his/her hands in front of the detector's sensor which will detect whether HWAMs are present on the subject's skin. In certain embodiments, the indicator can report a "pass" or "fail" reading based on the presence or absence, respectively, of the HWAM on or emanating from the subject's skin. The "pass/fail" information can be fed to a central computer, whereby a subject's compliance with hand hygiene measures can be determined.

In certain related embodiments, the identity ascertaining is operably connected to an entry means (e.g., a lock to a door). With such embodiments, the entry means will not permit the subject to enter or exit a location unless the detector has ascertained that the subject has performed appropriate hand hygiene measures. For example, a lock to a door to a patient's room will only disengage after a "pass" reading is communicated from the indicator after a subject has waved his/her hands in front of the detector.

Sensors

According to the subject invention, any one of the many commercially available off the shelf (COTS)-based analytical approaches for measurement of analytes in gaseous phase mediums can be used to detect and/or quantify HWAMs on or in close proximity to a subject's skin. These devices offer minimal cycle time, can detect multiple HWAMs, can work in almost any environment without special sample preparation or isolation conditions, and do not require advanced sensor design or cleansing between tests.

It is contemplated that the hand hygiene monitoring system of the invention may comprise at least one sensor, or a plurality of sensors, for capturing/detecting the desired HWAM data. Each sensor generates an output signal based on the presence of the HWAM(s) to an indicator. Examples of certain COTS-based approaches that can be used in accordance with the systems and methods described herein include, but are not limited to, high electron mobility transistors (HEMT), nuclear magnetic resonance (NMR), polymer based membranes-chemoresistive (Cyranose); polymer-surface acoustic wave (SAW) and electrochemical chemical array (Hazmatcad and Hazmatcad Plus); spectroscopy-based analysis; visible spectroscopy; UV spectroscopy; TIF TIFXP-1A Negative Corona Leak Detector; negative ion capture sensors; heated sensors/ceramic semiconductor sensors; infrared absorption; nuclear magnetic resonance spectroscopy; photoemission spectroscopy; Raman spectroscopy; Fourier transform spectroscopy—FTIR; time-resolved spectroscopy; flame spectroscopy; plasma emission spectroscopy; force spectroscopy; dielectric spectroscopy; circular dichroism spectroscopy; refractory indices; and the like. Other contemplated sensors include sensors based on microcantilevers, molecularly imprinted polymers, amplifying fluorescent polymers, and high electron mobility transistors. In a preferred embodiment, small scale (miniature) gas chromatography technology, which employs metal oxide (MOS) or other sensors, is used in accordance with the subject invention.

The invention preferably utilizes sensor technology, such as commercial devices known as "artificial" or "electronic" tongues or noses, to monitor HWAM presence and/or concentration on or in close proximity to a subject's skin. Electronic noses have been used mostly in the food, wine, and perfume industry where their sensitivity makes it possible to distinguish between odorous compounds. For example, electronic noses have been useful in distinguishing between grapefruit oil and orange oil in the perfume industry and in identifying spoilage in perishable foods before the odor is evident to the human nose. In a related embodiment, the sensor's particular resistor geometries can be selected to optimize the desired response to a particular HWAM being sensed. For example, a self-calibrating polymeric "electronic nose" system is suitable for use in accordance with the subject invention to analyze the skin of a subject for the presence of a HWAM.

A number of patents that describe gas sensor technology that can be used in the subject invention include, but are not limited to, the following: U.S. Pat. Nos. 7,171,312; 5,945,069; 5,918,257; 4,938,928; 4,992,244; 5,034,192; 5,071,770; 5,145,645; 5,252,292; 5,605,612; 5,756,879; 5,783,154; and 5,830,412; all of which are incorporated herein by reference in their entirety. Other sensors suitable for the present invention include, but are not limited to, metal-insulator-metal ensemble (MIME) sensors, cross-reactive optical microsensor arrays, fluorescent polymer films, surface enhanced Raman spectroscopy (SERS), diode lasers, selected ion flow tubes, metal oxide sensors (MOS), non-dispersive infrared spectrometer, bulk acoustic wave sensors, colorimetric tubes, functionalized microcantilevers, and infrared spectroscopy.

Recent developments in the field of detection that can also be used as sensors for the subject invention include, but are not limited to, gas chromatography, semiconductive gas sensors, mass spectrometers (including proton transfer reaction mass spectrometry), and infrared (IR) or ultraviolet (UV) or visible or fluorescence spectrophotometers (e.g., non-dispersive infrared spectrometer). For example, with semiconductive gas sensors, HWAMs cause a change in the electrical properties of semiconductor(s) by making their electrical resistance vary, and the measurement of these variations allows one to determine the concentration of HWAM(s). In another example, gas chromatography, which consists of a method of selective detection by separating the molecules of gas compositions, may be used as a means for analyzing HWAMs on or in close proximity to a subject's skin.

In accordance with the subject invention, sensors for detecting/quantifying HWAMs utilize a relatively brief detection time of around a few seconds. Other recent gas sensor technologies contemplated for use in a hand hygiene monitoring system of the present invention include apparatuses that utilize conductive-polymer gas-sensors ("polymeric"), aptamer biosensors, amplifying fluorescent polymer (AFP) sensors, or apparatuses having surface-acoustic-wave (SAW) gas-sensors.

Conductive-polymer gas-sensors (also referred to as "chemoresistors") have a film made of a conductive polymer sensitive to molecules of target (sometimes odorous) substances. Upon contact with target HWAM molecules, the electric resistance of the sensors changes, which provides an indication of the HWAM's presence. An advantage of this type of sensor is that it functions at temperatures close to room temperature. Different sensitivities for detecting different HWAMs can be obtained by modifying or choosing an alternate conductive polymer.

Responses of polymeric gas sensors to target HWAMs can be fully characterized using a combination of conventional gas sensor characterization techniques. For example, the sensor can be attached to a computer. The results can be displayed on the computer screen, stored, transmitted, etc. A data analyzer can compare a pattern of response to previously measured and characterized responses from known substances. The matching of those patterns can be performed using a number of techniques, including neural networks. The particular resistor geometries are selected to optimize the desired response to the particular HWAM being sensed.

Amplifying fluorescent polymer (AFP) sensors may be utilized in the present invention for detecting the presence of HWAMs on a subject's skin. AFP sensors are extremely sensitive and highly selective chemosensors that use amplifying fluorescent polymers. When target HWAMs bind to thin films of the polymers, the fluorescence of the film decreases. A single molecule binding event quenches the fluorescence of many polymer repeat units, resulting in an amplification of the quenching. The binding of HWAMs to the film is reversible, therefore the films can be reused.

Surface-acoustic-wave (SAW) sensors oscillate at high frequencies and generally have a substrate, which is covered by a chemoselective material. In SAW sensors, the substrate is used to propagate a surface acoustic wave between sets of interdigitated electrodes (e.g., to form a transducer). The chemoselective material is coated on the transducer. When a HWAM interacts with the chemoselective material coated on the substrate, the interaction results in a change in the SAW properties, such as the amplitude of velocity of the propagated wave. The detectable change in the characteristic wave is generally proportional to the mass load of the HWAM(s) (e.g., concentration of the HWAM on a subject's skin, which corresponds to the amount of handwashing agent used by the subject during a handwashing event).

Certain embodiments of the invention use known SAW devices, such as those described in U.S. Pat. Nos. 4,312,228 and 4,895,017. Other types of chemical sensors known in the art that use chemoselective coating applicable to the manufacture and operation of a hand hygiene monitoring system of the present invention include bulk acoustic wave (BAW) devices, plate acoustic wave devices, interdigitated microelectrode (IME) devices, optical waveguide (OW) devices, electrochemical sensors, and electrically conducting sensors.

In one embodiment, the sensor of the invention is based on surface acoustic wave (SAW) sensors. The SAW sensors preferably include a substrate with piezoelectric characteristics covered by a polymer coating, which is able to selectively absorb target HWAMs. SAW sensors oscillate at high frequencies and respond to perturbations proportional to the mass load of certain molecules. This occurs in the vapor phase on the sensor surface.
Indicator According to the subject invention, the indicator is capable of alerting the subject as well as other interested parties (such as patients, healthcare personnel, hygiene monitoring individuals, and/or in some instances health officials) of subject compliance/non-compliance with hand hygiene measures. In certain related embodiments, the detector system is also capable of tracking/analyzing compliance based on detected handwashing events, which is associated with detection of the HWAM from the subject's skin.

The results from a sensor are provided to the subject (or anyone else interested in the subject's hand hygiene) via an indicator. Contemplated indicators include a computer processor linked to the sensor technology in which visual, audible, and/or tactile results can be provided. The indicator can include a visual light display (such as various colored lights—green, yellow, and red), digital display panel, transportable read/write magnetic media such as computer disks and tapes which can be transported to and read on another machine, and printers such as thermal, laser or ink-jet printers for the production of a printed report or can be incorporated into the detector.

The indicator can provide the results to the subject via the detector itself or via external systems, such as facsimile, electronic mail, mail or courier service, or any other means of safely and securely sending data generated by the sensor. For example, in embodiments where the detector is located at a particular location, data generated by the sensor can be transmitted to a badge worn by the subject to light an LED on the badge. The LED can remain lit for a desired period of time to show others that the subject has recently performed handwashing. Interactive indicators are also contemplated by the present invention, such as an interactive voice response system, interactive computer-based indicator system, interactive telephone touch-tone system, or other similar system. The report provided to the subject may take many forms, including immediate communication regarding a handwashing event; a summary of analyses performed over a particular period of time; or detailed information regarding a handwashing event. Results may also be used to populate a laboratory database or a statistical database.

Operation of a Monitoring System

Figure 1:
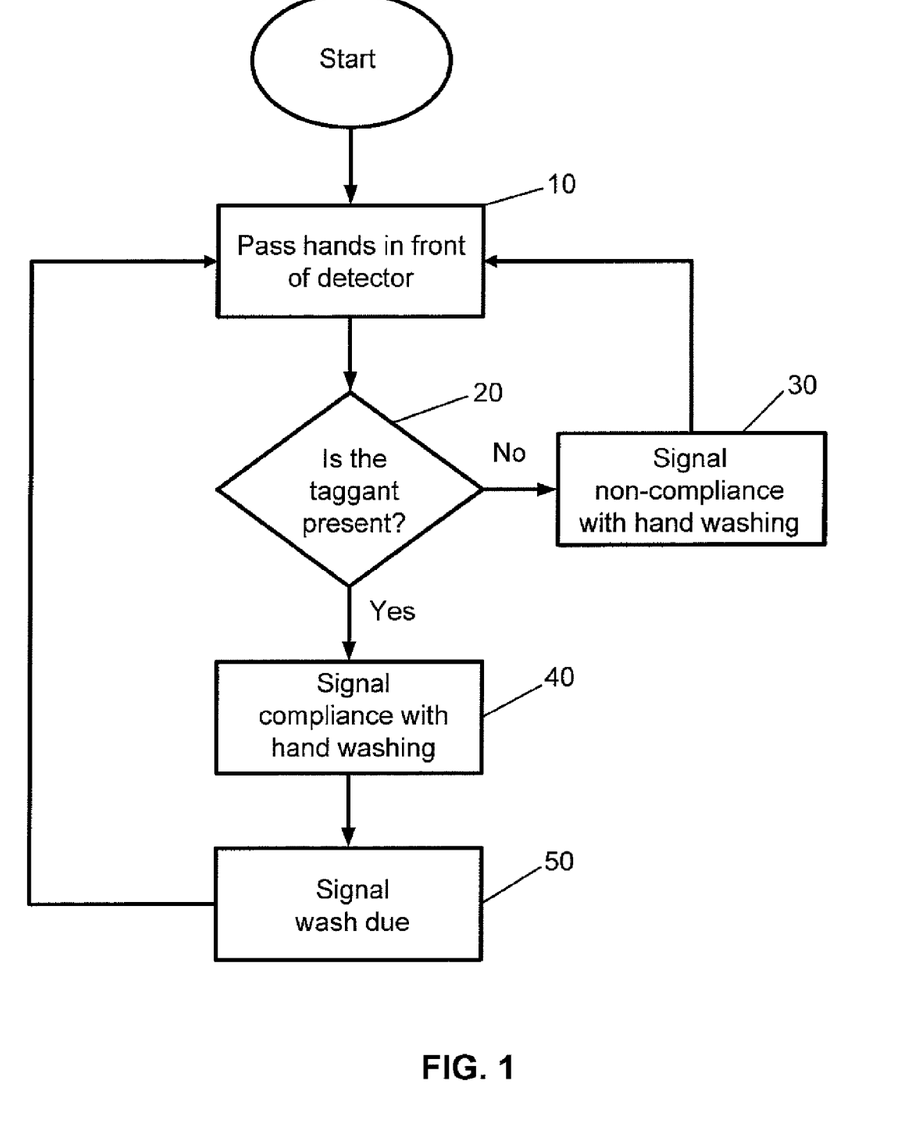
FIG. 1 is a flow chart showing operations that occur when using a detector of the invention.

As illustrated in FIG. 1, a method of using the hand hygiene monitoring system of the invention includes passing the subject's hands in close proximity to the detector 10 to detect the presence of any HWAMs 20; and communicating compliance or non-compliance with a handwashing event 30, 40, wherein HWAM detection is a surrogate indicator of a handwashing event. In certain embodiments, after a specific period, the detector notifies the subject (and any other interested party, such as a client, patient, co-worker, etc.) that another handwashing event is due 50.

In certain embodiments, the detector can "actively" detect HWAMs by including a means for directing/drawing air to the sensor(s) on the detector. One such embodiment includes a suction pump on the detector that can direct air (and HWAMs, if present) to the sensors. The suction pump can be activated by the individual before handwashing or automatically activated by a means for establishing subject identity (such as a badge, bracelet, radio-frequency identification chip, etc.). Other embodiments of the invention would function "passively" and would not require a suction pump to detect HWAMs on the skin.

HWAMs associated with handwashing are preferably identified by a portable, wearable detector. The detector would be worn on a lab coat or elsewhere on the person and would be activated at the time handwashing is commenced. After handwashing (either before or after drying), the HWAM would be detected emanating from the hands of the subject when they are passed in proximity of the sensor in the detector. The indicator, such as with a light with various colors, would be activated should a HWAM be detected by the sensor. Preferably, the indicator includes a green light indicating recently detected handwashing event; a yellow light indicating last handwashing event had occurred within a first specified period of time that is acceptable; and a red light indicating last handwashing event had occurred within second specified period of time that is unacceptable. Alternatively, since a red color may be misleading and have negative connotations to patients, the badge could turn colorless after a set period of time after handwashing.

In a method of use, after the subject has washed his/her hands with a handwashing agent of the invention, the subject waves his/her hands in front of a detector worn by the subject. The sensor in the detector senses the HWAMs on the subject's skin, which would be communicated by the indicator as a green light. After an acceptable period, such as 10-15 minutes after handwashing, the indicator light on the device would turn yellow. After 10-15 minutes, the light would turn red or colorless, indicating that the last handwashing event that occurred was about 20-30 minutes ago.

Figure 2:
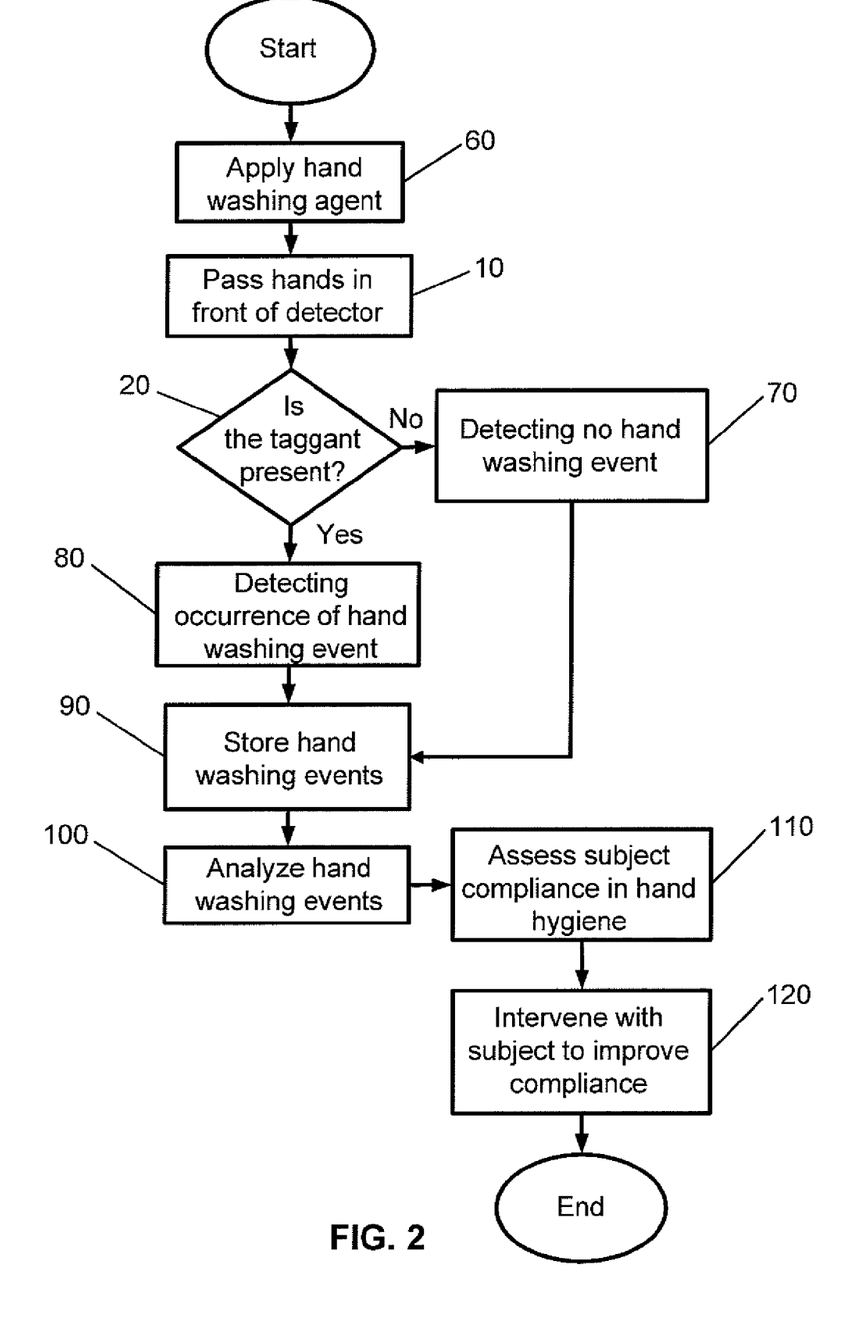
FIG. 2 is a flow chart showing operations that occur with certain embodiments of the invention.

Related methods for monitoring hand hygiene compliance can further include any one or combination of the following steps (see FIG. 2): applying handwashing agent to skin 60; detecting handwashing events 70, 80, storing 90 and/or analyzing 100 the detected handwashing events; assessing the subject's hand hygiene compliance based on the detected handwashing events 110; and intervening with the subject when appropriate to improve subject compliance 120.

In certain embodiments, in operation, the sensor will be used to identify a baseline spectrum for the subject prior to use of a handwashing agent that includes a taggant to generate the HWAM, if necessary. This will prove beneficial for the detection of the HWAM where possible interference from other odors (such as perfumes in lotions) is presented.

In another embodiment, the detector and a subject identification means, which automatically detects the identification/presence of an individual by a badge, RF-ID chip, etc., are mounted in close proximity to a handwashing station. When the subject approaches the subject identification means, it immediately begins a countdown process activating the detector, which must detect the presence of a HWAM within a finite period after the identification means is activated or the indicator will provide feedback locally and/or remotely that the subject has not washed his/her hands.

Remote Communication System

A further embodiment of the invention includes a communications device that will be interfaced to a monitoring system of the invention. The communications device will be able to transmit immediately or at prescribed intervals via standard communication transmittal means (e.g., via satellite communication) the data collected by the system of the invention. The communication of the data will allow the interested party (e.g., hygiene monitoring personnel) to be able to verify if the subject has complied in performing handwashing using a handwashing agent of the invention and/or if the appropriate amount of a handwashing agent is being used by the subject during handwashing.

The data transmitted from the detector can also be downloaded to a computer where the detected presence of the HWAM are stored in a database, and any deviations outside of the stored data is flagged so that a user could be notified of subject hand hygiene compliance. In one embodiment, the downloaded information pertains to number of times HWAM was detected (or HWAM levels/concentration) and deviations outside of a given number would be automatically flagged (e.g., alarm) so that a subject or other interested party (e.g., patient, physician, nurse) could address the lack of hand hygiene per suggestions provided by a computer processing unit connected to the sensor or per suggestions provided by health care personnel (e.g., hospital management personnel).

Following are examples that illustrate materials, methods, and procedures for practicing the invention. The examples are illustrative and should not be construed as limiting.

EXAMPLE 1

In one embodiment, a heathcare worker would dispense an adequate amount of hand soap or surgical scrub and vigorously wash the hands with water to release the encapsulated taggant to generate the HWAM. Alternatively, the microcapsules could be incorporated into "waterless" handwashing products. Prior to washing the hands, the healthcare worker would activate the detector, which would be worn in a conspicuous place so that patients could observe it, by means such as pushing a button, and then slowly wave the hands in front of the device after washing (either before or after drying). Activation of the device would result in samples of air being drawn into the device and analyzed for the presence of the HWAM. When the hands are slowly placed in front of the device, a sample of air (gas) containing the HWAM would be detected and a conspicuous light would turn from red or yellow to green. This light would remain green for a period of time (such as 10 minutes) so that the patient would be assured that the healthcare worker had washing his/her hands recently. A yellow or red indicator would signal to the patient that the healthcare worker needed to wash the hands before touching the patient.

EXAMPLE 2

The detector in certain preferred embodiments is best placed in close proximity to the handwashing site (e.g. a sink and soap, or a dispenser for waterless products such as alcohol-based gels or foams), rather than worn by the subject. It is clear that wearing of the detector by the subject will add additional cost that can be mitigated by the detector being positions at the point of hand cleansing (such as the case of a towel dispenser when water and soap are used). In such embodiments, a badge can be worn by the subject containing an indicator such as an LED that makes it apparent to anyone in proximity to the subject whether the subject has recently washed his/her hands. The badge in such embodiments can be a "passive" receiver and would not require the sophisticated electronics of a detector.

Mounting the detector in close proximity to the handwashing station has many advantages including the ability to link the detector to a computer system which identifies the individual who washed his/her hands and stores this information in a database which can be accessed to determine handwashing compliance.

For example, in a healthcare facility, each healthcare worker will wear a device capable of uniquely identifying them when they are in very close proximity to the detector so that other individuals who are present along with the healthcare worker who is washing his/her hands will not inadvertently be mis-identified as the individual washing his/her hands. Preferably this is done by the individual wearing a bracelet or similar device containing an identification means, such as an RFID chip, which identifies them only when they are in very close proximity to the detector. Alternatively the unique identifier can be incorporated into a badge, such as part of some newer systems that identify the location of healthcare workers within a healthcare facility.

With the detector mounted in proximity of the handwashing station, the indicator, such as a visual badge, audible sound, or combination thereof, will send a signal ONLY to the device worn by the individual who washed his/her hands, and not to other individuals in close proximity to the detector. Thus the detector must have the ability to discriminate the individual who washed his/her hands from other individuals present in the patient room or other healthcare providing area.

In order for the sensor to detect only the HWAM emanating from the hands of the individual who has just (or very recently) washed them, the hands should be placed a set distance from the sensor and gas samples drawn into the sensor. This distance can be precisely controlled by placing a screen or shield a set distance from the sensor or having beams of light form a specific pattern (such as an "X") on the hands of the individual who has washed his/her hands. Additionally, an activation means, such as a movement or position sensor can be used to turn on the detection system immediately before a sample of gas (air) is drawn into the sensor so the system does not have to remain active at all times. This is especially useful if the detection systems are deployed by handwashing stations that are not located in proximity to AC power and the detectors are battery operated. Since many sensors require very low power, power for the detection system could come from a solar array which powers the unit from ambient light.

EXAMPLE 3

At this point it is helpful to describe a complete cycle of use of the handwashing system in a hospital environment. Similar scenarios can occur in a physician's office, clinic, operating room, or any other healthcare environment. Similar applications can be used wherever it is important to document and encourage handwashing by workers, such as in food handling environments. In an exemplary embodiment, the cycle includes the following stages:

1. A transmitter worn by a healthcare worker, or a passive device worn by the worker that is detected by an active device mounted at the entrance to a patient room or other care area, identifies the presence of a particular healthcare worker and the system documents the time and date that the worker was in proximity to the detection system.
2. If the healthcare worker is NOT going to be in intimate contact with the patient and handwashing is NOT required, the device so indicates by documenting that handwashing events did NOT occur. These situations may be when the worker is merely visiting the patient or is having discussions with the family or when the healthcare worker is accompanying another healthcare worker and does not intend to examine the patient. These individuals will have badges that do NOT indicate a color (blank), thus indicating that they have not washed their hands and should NOT touch or be in close proximity to the patient or to devices that could be contaminated and pose a risk to the patient.
3. If the healthcare worker intends to examine the patient, he/she must wash his/her hands either with soap and water or with a water-free product. Upon completion of handwashing he/she must document handwashing by running his/her hand under a detector which can be turned on when it detects his/her RFID or other unique identifier, or by the hand triggering a signaling device to turn on the detector. When the detector detects the presence of the HWAM it sends a signal to the "indicator" worn by the healthcare worker and turns it to green. It can also cause the indicator to make an audible signal thus alerting the healthcare worker that the badge has been activated without having to specifically check the color change. When the healthcare worker is in close proximity to the patient, a device worn by the patient detects the presence of the healthcare worker's unique identifier and sends this information to the central database. Thus, the device worn by the patient is an active device, not a passive one, and only detects the presence of the healthcare worker when they are in close proximity, thus preventing the detection of other healthcare workers who are merely observing and are not in intimate contact with the patient. This device can be incorporated into a variety of vital signs monitors, such as pulse oximeter, which are almost ubiquitous in hospitals or into devices that uniquely identify the patient. Companies such as Hill-Rom have detection systems that determine the location and number of encounters healthcare workers have with patients, and are well known in the art.
4. This system also prevents a healthcare worker from coming into close proximity of other patients without handwashing in between. In a patient room with more than a single patient (multipatient rooms) the healthcare worker is required to wash his/her hands before touching EACH patient and this system will insure handwashing between patient encounters.
5. Another Center for Disease Control recommended safety measure is that the healthcare worker must again wash his/her hands upon leaving a particular room. This handwashing event will be detected as described above, and if the healthcare worker leaves without handwashing this will be detected by the active detector, such as is present in the Hill-Rom system, or by there being "absent" handwashing events, as compared to the number of patients encountered by the healthcare worker.

EXAMPLE 4

If is important to be sure that there are no false positives (detector indicates handwashing when it did not occur) or false negatives (detector does not indicate handwashing when if fact it did occur). False positives can be avoided by selecting HWAMs that do not persist on the hands. Particularly advantageous are fluorinated compounds that can be highly volatile and will have short persistence on the hands whether in a soap, or water-less gel or foam. Also, the limit of detection (LOD) of the detector can be set so that extremely low levels of HWAM do not set off the detector and indicate handwashing since the presence of very low levels of HWAM may be present in the atmosphere if multiple handwashings occur in a short period of time. Most healthcare facilities have adequate environmental air turnover to prevent this.

A false negative can be dealt with by the subject by running his/her hand under the detector a second time.

Another more time consuming but highly effective strategy to prevent both false positives and negatives is to require the subject to obtain a "baseline" sample before each episode of handwashing, against which a post-handwashing reading can be compared.

In view of the above, the present invention provides the capability of continuously, monitoring subject compliance in hand hygiene practices, using the detection of taggants in handwashing agents as a surrogate for a handwashing event.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A system for monitoring hand hygiene of a subject, the system comprising:
a handwashing agent comprising a taggant to generate a volatile or semi-volatile handwashing adherence marker, HWAM; a detector comprising a sensor; and an indicator operably connected to the sensor; wherein the sensor is capable of detecting the HWAM without physical contact of the hands of said subject with said detector, the indicator communicates information from the sensor regarding whether there has been an HWAM detection, said HWAM being detectable by said sensor on or emanating from the hands of a subject immediately or within a short period of time after a handwashing event utilizing said handwashing agent comprising said taggant, wherein said taggant in said handwashing agent is contained within hard particles, soft particles, or both; wherein said particles are microencapsulated particles housing taggants wherein said particles are made using microencapsulation techniques selected from the group consisting of coacervation, double emulsion (w/o/w), polymerization, co-extrusion capsule formulation, and air-suspension coating;
wherein said microencapsulated particles are made by double emulsion utilizing poly L-lactic acid (PLLA) dissolved in methylene chloride, and emulsified with an aqueous or other incompatible solvent containing said taggant.

2. The system according to claim 1 wherein said emulsion is adjusted to make a water in oil emulsion.

3. The system according to claim 2 wherein said emulsion is poured into a second aqueous or other incompatible solvent and air is bubbled through, which evaporates the organic solvent, causing the PLLA to encapsulate said taggant in a hard shell.

4. A system for monitoring hand hygiene of a subject, the system comprising: a handwashing agent comprising a taggant to generate a volatile or semi-volatile handwashing adherence marker, HWAM; a detector comprising a sensor; and an indicator operably connected to the sensor; wherein the sensor is capable of detecting the HWAM without physical contact of the hands of said subject with said detector, the indicator communicates information from the sensor regarding whether there has been an HWAM detection, said HWAM being detectable by said sensor on or emanating from the hands of a subject immediately or within a short period of time after a handwashing event utilizing said handwashing agent comprising said taggant, wherein said taggant in said handwashing agent is contained within hard particles, soft particles, or both;
wherein taggant is mixed with a surfactant and water with dissolved sugar to form particles in the form of an emulsion.

5. The system according to claim 4 wherein said emulsion is poured into a larger volume of a non-volatile organic, and air is bubbled through, resulting in particles containing taggant trapped within a sugar matrix formed upon evaporation of the water by the air.

6. The system according to claim 5 which, when suspended in an organic gel, the particles remain intact until they are exposed to water and rubbing caused by the washing of hands.

7. A system for monitoring hand hygiene of a subject, the system comprising: a handwashing agent comprising a taggant to generate a volatile or semi-volatile handwashing adherence marker, HWAM; a detector comprising a sensor; and an indicator operably connected to the sensor; wherein the sensor is capable of detecting the HWAM without physical contact of the hands of said subject with said detector, the indicator communicates information from the sensor regarding whether there has been an HWAM detection, said HWAM being detectable by said sensor on or emanating from the hands of a subject immediately or within a short period of time after a handwashing event utilizing said handwashing agent comprising said taggant, wherein
said taggant in said handwashing agent is contained within hard particles, soft particles, or both:
wherein a pressurized container is attached to a container of disinfecting liquid so that activation thereof releases the contained taggant into the other liquid.

8. A system for locating personnel in an enclosed facility having a plurality of spaced-apart stations, said system comprising:
(a) a separate indicator badge or tag for each of said personnel;
(b) at least one detector or monitor for detecting when one of said badges is located within a predetermined distance from one of said stations, and for reading information from the detected badge or tag at said station;
(c) each of said detectors or monitors including first and second wireless transmitters for transmitting first and second wireless signals, the signals having transmission velocities different from one another; and
(d) a device for detecting the difference in transmission times between said first and second signals and indicating when said difference is below a predetermined value;
wherein, in addition to confirming hand wash compliance, the system, comprises data sorting and selection algorithms for purposes of generating billing records based on the health-care worker location in relation to given patients;
comprising location detectors mounted near or onto patient beds, on wheelchairs, gurneys, and other internal hospital transportation patient-supporting devices for detecting the tag of each person who approaches the patient close enough to touch the patient or otherwise transmit pathogens to the patient;
wherein volatile acids or bases are made less volatile by forming salts, which then are released when the pH of the medium is changed during washing by loss of a volatile acid or base material which shifts the pH.

9. A system for monitoring hand hygiene of a subject, the system comprising: a handwashing agent comprising a taggant to generate a volatile or semi-volatile handwashing adherence marker, HWAM; a detector comprising a sensor; and an indicator operably connected to the sensor; wherein the sensor is capable of detecting the HWAM without physical contact of the hands of said subject with said detector, the indicator communicates information from the sensor regarding whether there has been an HWAM detection, said HWAM being detectable by said sensor on or emanating from the hands of a subject immediately or within a short period of time after a handwashing event utilizing said handwashing agent comprising said taggant, wherein said taggant in said handwashing agent is contained within hard particles, soft particles, or both;
    wherein said particles are microcapsules and: (a) water activates a mixture of dry sodium bicarbonate and dry calcium acetate to cause evolution of carbon dioxide to disrupt microcapsules;
    (b) osmotic pressure formed by water movement into an encapsulated salt disrupts a shell; (c) volatile acids are attached to a polymer with an ester bond Cleaved by esterases present naturally or delivered in a two part applicator.

10. A system for monitoring hand hygiene of a subject, the system comprising: a handwashing agent comprising a taggant to generate a volatile or semi-volatile handwashing adherence marker, HWAM; a detector comprising a sensor; and an indicator operably connected to the sensor; wherein the sensor is capable of detecting the HWAM without physical contact of the hands of said subject with said detector, the indicator communicates information from the sensor regarding whether there has been an HWAM detection, said HWAM being detectable by said sensor on or emanating from the hands of a subject immediately or within a short period of time after a handwashing event utilizing said handwashing agent comprising said taggant, wherein said taggant in said handwashing agent is contained within hard particles, soft particles, or both;
    wherein encapsulated halogenated compounds inside particles release taggants with physical gating mechanisms.

* * * * *

UNITED STATES PATENT AND TRADEMARK OFFICE
CERTIFICATE OF CORRECTION

PATENT NO.         : 8,525,666 B2                                           Page 1 of 1
APPLICATION NO.    : 12/599743
DATED              : September 3, 2013
INVENTOR(S)        : Melker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 725 days.

Signed and Sealed this
Fifteenth Day of September, 2015

Michelle K. Lee
*Director of the United States Patent and Trademark Office*